United States Patent
Hendrix, III et al.

(10) Patent No.: US 9,538,751 B2
(45) Date of Patent: Jan. 10, 2017

(54) CANOLA SEED TREATMENT COMPOSITION AND METHOD

(71) Applicant: Dow AgroSciences LLC, Indianapolis, IN (US)

(72) Inventors: William H. Hendrix, III, Indianapolis, IN (US); Gary C. Turnbull, Winnipeg (CA)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

(21) Appl. No.: 14/206,379

(22) Filed: Mar. 12, 2014

(65) Prior Publication Data

US 2014/0274687 A1    Sep. 18, 2014

Related U.S. Application Data

(60) Provisional application No. 61/781,062, filed on Mar. 14, 2013.

(51) Int. Cl.
| | | |
|---|---|---|
| *A01N 43/22* | (2006.01) | |
| *A01N 25/00* | (2006.01) | |
| *A01N 43/36* | (2006.01) | |
| *A01N 43/653* | (2006.01) | |
| *A01N 51/00* | (2006.01) | |

(52) U.S. Cl.
CPC .............. *A01N 43/22* (2013.01); *A01N 25/00* (2013.01); *A01N 43/36* (2013.01); *A01N 43/653* (2013.01); *A01N 51/00* (2013.01)

(58) Field of Classification Search
None
See application file for complete search history.

(56) References Cited

U.S. PATENT DOCUMENTS

| | | | |
|---|---|---|---|
| 6,660,690 B2 * | 12/2003 | Asrar et al. .................. 504/100 |
| 8,293,680 B2 | 10/2012 | Lindholm et al. | |
| 2011/0269804 A1 | 11/2011 | Cassayre et al. | |
| 2011/0275518 A1 | 11/2011 | Marques et al. | |

FOREIGN PATENT DOCUMENTS

| | | |
|---|---|---|
| WO | WO 2011014720 A1 * | 2/2011 |
| WO | 2012080415 A1 | 6/2012 |
| WO | 2013015993 A1 | 1/2013 |

OTHER PUBLICATIONS

"Wide Range of Seed Weights" Canola Watch [online] (Apr. 25, 2012) Issue 9, retrieved from the internet on Jun. 27, 2015 from URL<http://www.canolawatch.org/2012/04/25/wide-range-of-seed-weights/.*
International Search Report and Written Opinion, Jul. 7, 2014, pp. 1-8, International Searching Authority, Alexandria, Virginia.

* cited by examiner

*Primary Examiner* — Abigail Fisher
*Assistant Examiner* — Daniel Branson
(74) *Attorney, Agent, or Firm* — Yung H. Lee; Carl D. Corvin

(57) ABSTRACT

Canola seed treated with spinosad controls flea beetle.

3 Claims, No Drawings

CANOLA SEED TREATMENT COMPOSITION AND METHOD

CROSS REFERENCE TO RELATED APPLICATIONS

This application claims the benefit of U.S. Provisional Patent Application Ser. No. 61/781,062 filed Mar. 14, 2013, the entire disclosure of which is hereby expressly incorporated by reference.

FIELD OF THE INVENTION

The present invention relates to a seed treatment method for canola seeds.

BACKGROUND

The importance of using an insecticide seed treatment for protection against flea beetles in canola production is well known. (see, e.g., Knodel et al. 2006 Insecticide Efficacy against Flea Beetles on Canola Trial A., www.ag.ndsu.edu/archive/langdon/06data/fbsyngenta06.pdf). HELIX® (thiamethoxam), GAUCHO®600 (600 g/L imidacloprid), and PONCHO®600 (600 g/L clothianidin) insecticide seed treatments are registered for use on canola.

U.S. Pat. No. 6,583,088 discloses use of spinosad for treating seed and plant propagation material.

There remains a need for insecticide seed treatments for canola seed that provide improved performance.

SUMMARY OF THE INVENTION

In some embodiments, the invention provides a method of protecting canola seeds which comprises treating the seeds with spinosad.

In some embodiments the invention provides a method of protecting canola seeds which comprises treating the seeds with a combination of spinosad and one or more additional systemic insecticides.

In some embodiments, the invention provides a method of protecting canola seeds which comprises treating the seeds with a combination comprising spinosad and one or more fungicides.

In some embodiments, the invention provides canola seed that has been treated with spinosad.

DETAILED DESCRIPTION OF THE INVENTION

Definitions

As used herein, the following terms have the indicated meanings:

The term "spinosad" refers to a fermentation product comprising a combination of the spinosyn factors spinosyn A and spinosyn D, where spinosyn A comprises 50-95% and spinosyn D comprises 50-5% of the combination. Spinosad may also contain minor amounts of other spinosyn factors. Its activity and applications are summarized in Tomlin, C., ed. A World Compendium The Pesticide Manual. 15$^{th}$ ed. Alton: BCPC Publications, 2009 (hereafter "*The Pesticide Manual*"). Additional information regarding spinosad is found in "Compendium of Pesticide Common Names" located at http://www.alanwood.net/pesticides/index.html as of the filing date of this document.

The term "clothianidin" refers to [C(E)]-N-[(2-chloro-5-thiazolyl)methyl]-N'-methyl-N"-nitroguanidine, an insecticide. Its structure, activity and applications are summarized in *The Pesticide Manual*.

The term "difenoconazole" refers to 1-[2-[2-chloro-4-(4-chlorophenoxy)phenyl]-4-methyl-1,3-dioxolan-2-ylm-ethyl]-1H-1,2,4-triazole, a fungicide. Its structure, activity and applications are summarized in *The Pesticide Manual*.

The term "fludioxonil" refers to 4-(2,2-difluoro-1,3-benzodioxol-4-yl)-1H-pyrrole-3-carbonitrile, a fungicide. Its structure, activity and applications are summarized in *The Pesticide Manual*.

The term "metalaxyl-M" refers to methyl N-(2,6-dimethylphenyl)-N-(methoxyacetyl)-D-alaninate, a fungicide. Its activity and applications are summarized in *The Pesticide Manual*.

The term "thiamethoxam" refers to 3-[(2-chloro-5-thiazolyl)methyl]tetrahydro-5-methyl-N-nitro-4H-1,3,5-oxadi-azin-4-imine, an insecticide. Its structure, activity and applications are summarized in *The Pesticide Manual*.

The term "HELIX® XTra Seed Treatment" refers to a seed treatment product of Syngenta Crop Protection that contains, as active ingredients: thiamethoxam, difenoconazole, metalaxyl-M and S-isomer, and fludioxonil.

The term "imidacloprid" refers to (2E)-1-[(6-chloro-3-pyridinyl)methyl]-N-nitro-2-imidazolidinimine, a systemic insecticide. Its structure, activity and applications are summarized in *The Pesticide Manual*.

Methods for Treating Canola Seeds

In some embodiments of the invention, canola seed is treated with from about 0.1 to about 1 mg/seed of spinosad. In some embodiments, canola seed is treated with from about 0.2 to about 0.6 mg/seed of spinosad.

In some embodiments of the invention, canola seed is treated with a combination of spinosad and at least one other systemic insecticide. The other insecticide can be any systemic insecticide approved for treatment of canola seed. Non-limiting examples include thiamethoxam, imidacloprid, and clothianidin. In a certain embodiment of the invention canola seed is treated with a combination of spinosad, and thiamethoxam.

In some embodiments of the invention, canola seed is treated with a combination of spinosad and at least one fungicide. The fungicide can be any fungicide approved for treatment of canola seed. Non-limiting examples include difenoconazole, metalaxyl-M isomer and fludioxonil. In some embodiments, canola seed is treated with a combination of spinosad, difenoconazole, metalaxyl-M isomer and fludioxonil.

In some embodiment of the invention, canola seed is treated with a combination of spinosad, at least one additional systemic insecticide, and at least one fungicide. In some embodiments, canola seed is treated with spinosad, thiamethoxam, difenoconazole, metalaxyl-M isomer and fludioxonil.

Equipment and protocols for treating seed are well known in the art, and are described, e.g., in US 2011/0263429, which is incorporated herein by reference.

EXAMPLES

Example 1

Field Efficacy Trial for Canola Seed Treatment

Untreated canola seed, canola seed treated with standard HELIX® XTra Seed Treatment alone, canola seed treated with standard HELIX® XTra Seed Treatment plus 0.2 mg ai/seed of spinosad, and canola seed treated with standard HELIX® XTra Seed Treatment plus 0.6 mg ai/seed of spinosad were evaluated at intervals in small plot trials for damage caused by flea beetle.
Results of the trial are given in Table 1.

TABLE 1

Leaf Damage Caused By Flea Beetle, % Visual

| Treatment | 14 DAP | 20 DAP | 36 DAP |
|---|---|---|---|
| HELIX ® XTra | 23.4b | 4.1a | 11 |
| HELIX ® XTra plus spinosad 0.2 mg ai/seed | 14.1c | 4.3a | 4.4c |
| HELIX ® XTra plus spinosad 0.6 mg ai/seed | 10.9cd | 2.3a | 5.2c |
| UNTREATED | 93.1a | 9.8a | 19.7a |

DAP = days after planting
Means followed by the same letter do not significantly differ (P = .05, Student-Newman-Keuls)

What we claim is:

1. A method of treating canola seed to protect canola from flea beetle damage which comprises applying to the canola seed a combination of spinosad and a seed treatment composition comprising thiamethoxam, difenoconazole, metalaxyl-M isomer and fludioxonil, wherein the spinosad is applied to the canola seed at a rate of about 0.6 mg/seed.

2. A treated canola seed comprising thiamethoxam, difenoconazole, metalaxyl-M isomer, fludioxonil and about 0.6 mg/seed of spinosad.

3. A method of treating canola seed to protect canola from flea beetle damage which comprises applying to the canola seed a combination of spinosad and a seed treatment composition comprising thiamethoxam, difenoconazole, metalaxyl-M isomer and fludioxonil, wherein the spinosad is applied to the canola seed at a rate of about 0.2 mg/seed.

* * * * *